United States Patent
Poche

[11] Patent Number: 5,932,437
[45] Date of Patent: Aug. 3, 1999

[54] CONTROL OF LYME DISEASE SPIROCHETE

[75] Inventor: Richard M. Pochè, Ft. Collins, Colo.

[73] Assignee: Genesis Laboratories, Inc., Wellington, Colo.

[21] Appl. No.: 09/059,127

[22] Filed: Apr. 13, 1998

[51] Int. Cl.⁶ .............................. C12Q 1/18; C12Q 1/00
[52] U.S. Cl. .............................. 435/32; 435/4; 552/203; 540/331; 536/7.2
[58] Field of Search ................. 435/32, 4; 552/203; 540/331; 536/7.2

[56] References Cited

U.S. PATENT DOCUMENTS 5,262,173  11/1993  Sheth et al. .............................. 435/32

OTHER PUBLICATIONS

Moody et al; Antimicrobial Agents and Chemotherapy; V. 38, No. 7, pp. 1567–1572; Jul. 1994.

Johnson et al; Antimicrobial Agents and Chemotherapy; V31 (2), pp. 164–167, Feb. 1987.

*Primary Examiner*—Louise N. Leary
*Attorney, Agent, or Firm*—Dean P. Edmundson

[57] ABSTRACT

A method is described for controlling the spread of Lyme Disease spirochete from rodents which have been infected. The method involves orally administering to the rodents a composition which includes an antibiotic (e.g., tetracycline) which is capable of killing the spirochete. Bait compositions are described which include an antibiotic. The bait compositions may be solid or liquid.

6 Claims, No Drawings

CONTROL OF LYME DISEASE SPIROCHETE

FIELD OF THE INVENTION

This invention relates to methods and techniques for controlling Lyme Disease spirochete in rodents.

BACKGROUND OF THE INVENTION

In recent times, Lyme Disease has emerged as an increasing public health threat. The Center for Disease Control has reported that the number of Lyme Disease cases has increased steadily from 1982 to 1995 with 47 of 50 states reporting at least one case of Lyme Disease. In the United States, three ticks of the Ixodes genus, *Ixodes scapularis* and *Ixodes dammini* in the East and *Ixodes pacificus* in the West commonly carry the spirochete that causes the disease and are in a two year enzootic cycle with rodents and deer.

There has not heretofore been described an effective technique for controlling the Lyme disease spirochete *Borrelia burgdorferi* in rodents.

SUMMARY OF THE INVENTION

In accordance with the present invention, it has been discovered that spirochete infection in rodents can be cured by the use of baits which have been treated with an antibiotic. Accordingly, the present invention provides a method for interrupting the enzootic cycle to thereby control the spread of Lyme Disease spirochete. The method involves orally administering to rodents a composition containing an effective amount of an antibiotic of the type which is capable of killing said spirochete.

Using the technique of this invention, a bait composition which has been treated to include a suitable antibiotic material can be placed in the wild where rodents can feed on it. Ingestion of the composition by rodents which have been infected results in the elimination of the spirochete bacterium.

Other features and advantages of the invention will be apparent from the following detailed description.

DETAILED DESCRIPTION OF THE INVENTION

The method and technique of this invention involve preparing a bait composition which can be placed in the wild in areas where rodents are located and which may be infected with the Lyme Disease spirochete. The bait should be provided in amounts of about 200 grams in protected bait stations or in places which are protected from children, pets, and wildlife other than rodents.

Preferred compositions include a palatable feed mixture containing at least about 500 ppm of a suitable antibiotic such as tetracycline or any other antibiotic which is capable of killing the spirochete. Other such suitable antibiotics useful in this invention include, for example, doxycycline, erythromycin, azithromycin, amoxicillin, minocycline, metronidazole, as well as their salts and derivatives. Mixtures of antibiotics may also be used.

The amount of antibiotic in the composition is preferably in the range of about 100 ppm to about 1500 ppm or even greater concentrations if necessary, depending upon the particular antibiotic used. When using a tetracycline salt (e.g., the hydrochloride salt), it is preferred for a rodent to ingest at least about 50 mg per day per kilogram of body weight. The bait may comprise a water-based composition with the antibiotic dissolved in the water or suspended in palatable solvent.

EXAMPLE 1

A bait composition was prepared which included the following ingredients in the amounts stated:

| | |
|---|---|
| Mixed grains | 1970.00 g. |
| Corn oil | 20.00 g. |
| Confectioner's sugar | 9.50 g. |
| Tetracycline | 0.50 g. |

The tetracycline and confectioner's sugar were mixed thoroughly in a plastic bag. The mixed grains were placed under a Hobart mixer and mixed at a moderate speed. The corn oil was slowly added, followed by the antibiotic/sugar mixture. The composition was allowed to mix for approximately 15 minutes. The concentration of tetracycline in the final composition was 250 ppm.

EXAMPLE 2

A bait composition was prepared using the same ingredients and procedure as described in Example 1, except that the amount of tetracycline used was 1.0. gram and the amount of sugar used was 9.0 grams. The concentration of tetracycline in the final composition was 500 ppm.

EXAMPLE 3

A control composition was prepared using the same ingredients as stated in Example 1, except that no tetracycline was included.

EXAMPLE 4

The diet compositions described in Examples 1–3 were fed separately on a no-choice basis to separate groups of laboratory mice (Swiss-Webster) infected with the Lyme Disease spirochete *Borrelia burgdorferi*.

Eleven mice (ten study and one control) were used for each test composition. The mice chosen had been previously infected with *B. burgdorferi* by subcutaneous injection followed by a 21-day incubation period. To confirm the mice were positive for the spirochete, a modified ear punch biopsy was performed (Sinsky and Piesman 1989, J. of Clin. Micro. 27:1723–1727, CDCa 1997) on each mouse and the biopsy incubated in modified BSK-H media (CDCb) for 7 days and viewed under dark field microscopy. The prepared diets were fed to individually housed mice on a no-choice basis and water was offered ad libitum. The control mice were offered an identical diet minus the active ingredient. Consumption was recorded each day and additional feed was added. Diet was presented to the mice for seven consecutive days. On the day following the last day feed was offered, mice were anesthetized with methoxyflurane and ear punch biopsy was performed. The biopsies were incubated in modified BSK-H media for seven days at 34±1° C. Dark field microscopy was then performed on an American Optics 1031 microscope with an American Optics dark field 1096 condenser to determine the presence of spirochetes. Cultures were considered positive if spirochete growth occurred within five weeks of inoculation (Wilske and Preac-Mursic 1993), viewing the cultures at seven-day increments. A slide was considered negative if no spirochetes were found after searching 100 fields at 400× (Ginsberg and Ewing, J. of Med. Entomology, 26:183–189, 1989).

TABLE 1

TREATMENT LEVEL 1 RESULTS
TETRACYCLINE 250 µg/g

| | |
|---|---|
| MEAN BAIT CONSUMPTION (g) | 30.7 ± 8.5 |
| MEAN TETRACYCLINE INTAKE PER DAY (mg) | 1.1 ± 0.3 |
| NUMBER AND PERCENTAGE OF MICE TESTING NEGATIVE FOR SPIROCHETE | 9/10 (90%) |

TABLE 2

TREATMENT LEVEL 2 RESULTS
TETRACYCLINE 500 µg/g

| | |
|---|---|
| MEAN BAIT CONSUMPTION (g) | 32.8 ± 9.3 |
| MEAN TETRACYCLINE INTAKE PER DAY (mg) | 2.3 ± 0.7 |
| NUMBER AND PERCENTAGE OF MICE TESTING NEGATIVE FOR SPIROCHETE | 10/10 (100%) |

Other variants are possible without departing from the scope and spirit of this invention.

What is claimed is:

1. A method for controlling the spread of Lyme disease spirochete from rodents which have been infected therewith, the method comprising the step of orally administering to said rodents in the wild a composition containing an effective amount of an antibiotic of the type which is capable of killing said spirochete; wherein said antibiotic is selected from the group consisting of tetracycline, doxycycline, erythromycin, azithromycin, minocycline, metronidazole, or a salt or derivative thereof; wherein said composition additionally comprises grain and a sugar.

2. The method in accordance with claim 1, wherein the antibiotic is tetracycline or a salt or derivative thereof.

3. The method in accordance with claim 1, wherein said antibiotic is present in said composition in an amount of at least about 0.025% by weight.

4. The method in accordance with claim 1, wherein said composition is aqueous.

5. A method for killing Lyme Disease spirochete present in rodents in the wild comprising the step of feeding said rodents a comprising an antibiotic of a type capable of killing said spirochete; wherein said antibiotic is selected from the group consisting of tetracycline, doxycycline, erythromycin, azithromycin, minocycline, metronidazole, or a salt or derivative thereof; wherein said composition additionally comprises grain and sugar.

6. The method in accordance with claim 5, wherein said composition is aqueous.

* * * * *